(12) United States Patent
Okamoto et al.

(10) Patent No.: US 10,512,889 B2
(45) Date of Patent: Dec. 24, 2019

(54) MICROREACTOR

(71) Applicant: Ushio Chemix Corporation, Kakegawa-shi (JP)

(72) Inventors: Kazuo Okamoto, Omaezaki (JP); Masanori Tsutsui, Omaezaki (JP)

(73) Assignee: Ushio Chemix Corporation, Kakegawa-shi (JP)

(*) Notice: Subject to any disclaimer, the term of this patent is extended or adjusted under 35 U.S.C. 154(b) by 0 days.

(21) Appl. No.: 16/064,679

(22) PCT Filed: Dec. 22, 2016

(86) PCT No.: PCT/JP2016/088543
§ 371 (c)(1),
(2) Date: Jun. 21, 2018

(87) PCT Pub. No.: WO2017/111119
PCT Pub. Date: Jun. 29, 2017

(65) Prior Publication Data
US 2019/0009242 A1    Jan. 10, 2019

(30) Foreign Application Priority Data
Dec. 25, 2015   (JP) .................................. 2015-254118

(51) Int. Cl.
*B01J 19/00*     (2006.01)
*B81B 1/00*     (2006.01)
(Continued)

(52) U.S. Cl.
CPC ....... *B01J 19/0093* (2013.01); *B01J 19/0046* (2013.01); *B81B 1/00* (2013.01);
(Continued)

(58) Field of Classification Search
CPC .... B01J 19/00; B01J 19/0046; B01J 19/0093; B01J 2219/00781; B01J 2219/00889;
(Continued)

(56) References Cited

U.S. PATENT DOCUMENTS 8,067,653 B2 * 11/2011 Bressler ................ C07C 1/2078
44/300
8,230,877 B2    7/2012 Roberge et al.
(Continued)

FOREIGN PATENT DOCUMENTS

JP   2004190614 A   7/2004
JP   2006223967 A   8/2006
(Continued)

*Primary Examiner* — Natasha E Young
(74) *Attorney, Agent, or Firm* — The Webb Law Firm

(57) ABSTRACT

Provided is a microreactor which can be produced at a lower cost. The microreactor has a transfer means for transferring a liquid raw material using the pressure of a gas. The microreactor has a raw material tank for storing the liquid raw material. The transfer means for transferring a liquid raw material can transfer the liquid raw material stored in the raw material tank using the pressure of a gas in the raw material tank. A pipe which connects the raw material tank and the next device is preferably provided with a small diameter portion.

19 Claims, 8 Drawing Sheets

(51) Int. Cl.
*G01N 37/00* (2006.01)
*F04F 1/06* (2006.01)

(52) U.S. Cl.
CPC .............. *F04F 1/06* (2013.01); *G01N 37/00* (2013.01); *B01J 2219/00813* (2013.01); *B01J 2219/00869* (2013.01); *B01J 2219/00889* (2013.01); *B01J 2219/00963* (2013.01)

(58) Field of Classification Search
CPC ...... B01J 2219/0081; B01J 2219/00813; B01J 2219/00851; B01J 2219/00869; B01J 2219/0095–00954; B01J 2219/00963; B81B 1/00; F04F 1/00; F04F 1/06; G01N 37/00
See application file for complete search history.

(56) References Cited

U.S. PATENT DOCUMENTS

| | | | |
|---|---|---|---|
| 2005/0019213 A1 | 1/2005 | Kechagia et al. | |
| 2011/0008215 A1 | 1/2011 | Elizarov et al. | |
| 2011/0030809 A1 | 2/2011 | Ying et al. | |
| 2015/0217255 A1 | 8/2015 | Asano | |

FOREIGN PATENT DOCUMENTS

| | | |
|---|---|---|
| JP | 2006272276 A | 10/2006 |
| JP | 2006524797 A | 11/2006 |
| JP | 2007136253 A | 6/2007 |
| JP | 2008287429 A | 11/2008 |
| JP | 2009115821 A | 5/2009 |
| JP | 2009229262 A | 10/2009 |
| JP | 2010094660 A | 4/2010 |
| JP | 2010096655 A | 4/2010 |
| JP | 201113208 A | 1/2011 |
| JP | 2011036773 A | 2/2011 |
| JP | 2011517774 A | 6/2011 |
| JP | 2011156539 A | 8/2011 |
| JP | 2012256332 A | 12/2012 |
| JP | 2014217823 A | 11/2014 |
| JP | 2015120642 A | 7/2015 |
| WO | 2006043642 A1 | 4/2006 |

\* cited by examiner

MICROREACTOR

CROSS-REFERENCE TO RELATED APPLICATIONS

This application is the United States national phase of International Application No. PCT/JP2016/088543 filed Dec. 22, 2016 and published as WO 2017/111119, and claims priority to Japanese Patent Application No. 2015-254118 filed Dec. 25, 2015, the disclosures of which are hereby incorporated in their entirety by reference.

FIELD OF THE INVENTION

The present invention relates to a microreactor.

BACKGROUND ART

A microreactor has attracted attention as a reactor which substitutes for a conventional batch reactor, and various studies are being made on the microreactor. The "microreactor" is a general term for flow-type reaction apparatuses, of which the space scale of a reaction system is, for example, some micrometers, wherein a chemical or biochemical reaction is conducted in the reaction system. The microreactor has a transport path for a substance used in a reaction. The transport path has an inner diameter of, for example, some micrometers. In the microreactor, a plurality of substances can be efficiently mixed to cause a reaction. Further, the reaction can proceed uniformly at a constant temperature. Therefore, by using the microreactor, not only can the reaction selectivity be improved, but also the reaction rate can be increased. Further, it is said that the microreactor can be more easily scaled up than a conventional batch reactor from the laboratory scale to the production process scale. However, the microreactor has a high production cost as well as a lot of technical problems. For this reason, not many microchemical plants aimed for production have been realized.

The microreactor has lower productivity than that of a conventional batch reactor. For increasing the production of a microchemical plant, a method called numbering-up is studied. The numbering-up is a method of arranging a plurality of microreactors in parallel.

The numbering-up can be realized by arranging the same many apparatuses having a pump in parallel. The numbering-up method has a problem in that the production cost for the apparatus is high. This method is advantageous in that the process can be scaled up from the laboratory scale to the production scale without changing, e.g., the reaction conditions, and hence is easily industrialized.

Patent document 1 has a description of a numbering-up method in which a channel is branched. This method is a method in which a liquid raw material fed from a pump is distributed to a plurality of branched channels and mixers are arranged in parallel.

Patent document 2 has a description of a method in which a liquid is uniformly distributed to a plurality of microreactors without using a branched pipe.

Patent document 3 has a description of a microchannel reactor comprising a plurality of stacked channel units.

Patent document 4 has a description of a microreactor which is aimed at reducing the microchemical plant in cost and size.

PRIOR ART REFERENCES

Patent Documents

Patent document 1: JP 2007-136253A
Patent document 2: JP 2011-36773A
Patent document 3: JP 2014-217823A
Patent document 4: JP 2010-94660A

SUMMARY OF THE INVENTION

Problems to be Solved by the Invention

With respect to the numbering-up in which a channel is branched, it is said that it is difficult to flow a liquid raw material evenly into the many channels. Further, when one channel is plugged, a change of the flow rate is caused in the other channels, and therefore it is necessary to prevent the channels from being plugged. Moreover, there is a disadvantage in that monitoring of the channels must be made all the time to check whether each channel is plugged.

As mentioned above, the numbering-up achieved by branching a channel poses a number of technical problems to be solved. Therefore, numbering-up made by arranging apparatuses in parallel can be more easily industrialized. However, the numbering-up of this type causes the production cost for the apparatus to be extremely high, and therefore realization of a microreactor which enables numbering-up at a lower cost is desired.

Factors that determine the production cost of a microreactor include the price and performance of a pump. Generally, in a microreactor, as a means for transferring a substance to be reacted (a liquid raw material and/or a solution of a raw material), a syringe pump or a plunger pump is used.

The syringe pump has no pulsation, but, for conducting a continuous operation, two or more syringe pumps are needed per system. For precisely controlling the flow rate, an expensive syringe pump system is needed. Further, there is a danger that the syringe deteriorates during the continuous operation to cause a leak of liquid or a damage, and therefore, when a water-prohibitive reagent is transferred, particularly care must be taken.

It is easy to perform a continuous operation by the plunger pump, but, when the plunger pump has a single piston, pulsation is markedly large so that dispersion is caused in the reaction conditions. For this reason, it is necessary to use an expensive twin or triple pump having two or three pistons connected together.

In view of the above-mentioned problems, the present invention has been made, and an object of the present invention is to provide a microreactor which can be produced at a lower cost.

Means for Solving the Problems

The means for solving the problems is the following invention.

(1) A microreactor which has a transfer means for transferring a liquid raw material using the pressure of a gas.

(2) The microreactor according to item (1) above, which has a raw material tank for storing the liquid raw material, wherein the transfer means transfers the liquid raw material stored in the raw material tank using the pressure of a gas in the raw material tank.

(3) The microreactor according to item (2) above, which has a gas feeding means for feeding a gas into the raw material tank.

(4) The microreactor according to item (2) or (3) above, which has a pressure regulating means for regulating the pressure of the gas in the raw material tank.

(5) The microreactor according to any one of items (2) to (4) above, wherein the raw material tank comprises a pressure tank.

(6) The microreactor according to any one of items (2) to (5) above, which has a mixer for mixing the liquid raw material and another raw material with each other, wherein a pipe which connects the raw material tank and the mixer is provided with a small diameter portion.

(7) The microreactor according to item (6) above, wherein the small diameter portion comprises a tube having an inner diameter smaller than the inner diameter of a pipe positioned upstream and/or downstream of the tube.

(8) The microreactor according to item (6) or (7) above, wherein the pressure in a pipe which connects the raw material tank and the small diameter portion is 1.5 MPa or less.

(9) The microreactor according to any one of items (6) to (8) above, which has a plurality of the raw material tanks, wherein the liquid raw materials transferred from the raw material tanks are mixed by the mixer.

(10) The microreactor according to any one of items (1) to (9) above, wherein the gas is nitrogen.

(11) A microchemical plant comprising a plurality of the microreactors according to any one of items (1) to (10) above, wherein the microreactors are connected in parallel.

(12) A microchemical plant comprising the microreactor according to any one of items (1) to (10) above, wherein a plurality of channels are connected to the raw material tank.

Effects of the Invention

According to the present invention, it is possible to provide a microreactor which can be produced at a lower cost.

MODE FOR CARRYING OUT THE INVENTION

<First Embodiment>

Figure 1:
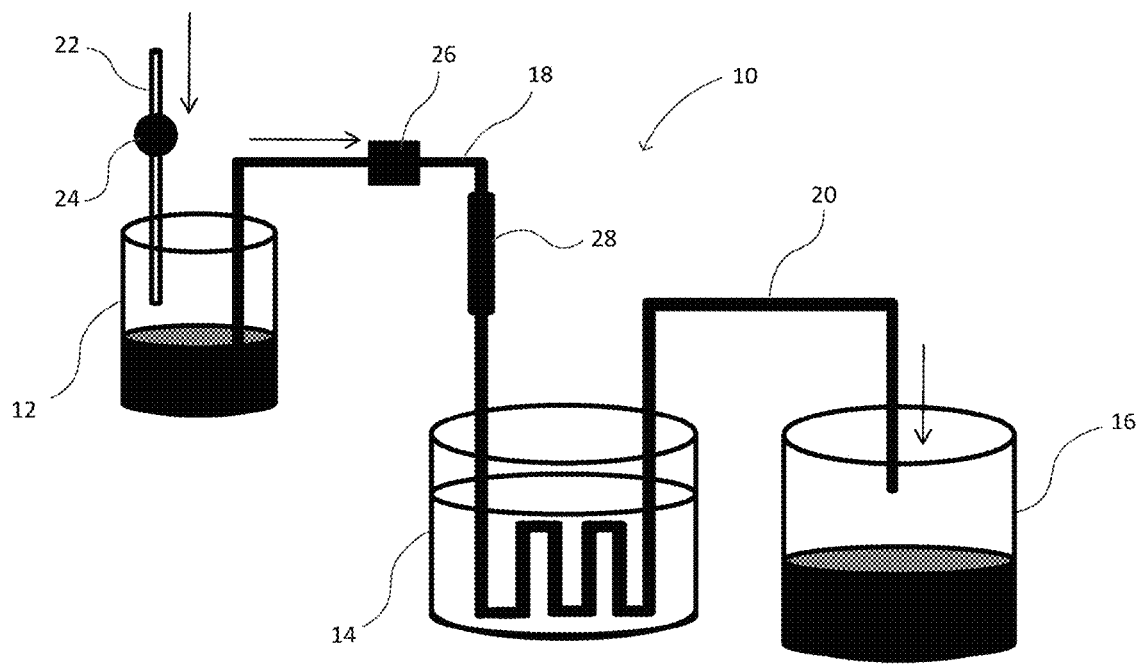
FIG. 1 shows a flow of the microreactor according to the first embodiment.

Hereinbelow, the first embodiment of the present invention will be described in detail with reference to the drawing.

FIG. 1 shows a flow of the microreactor according to the first embodiment.

As shown in FIG. 1, microreactor 10 according to the first embodiment has raw material tank 12, constant temperature bath 14, and reaction product tank 16. Raw material tank 12 is a tank for storing a liquid raw material. Constant temperature bath 14 is a bath for heating the liquid raw material. A reaction product obtained by heating the liquid raw material is stored in reaction product tank 16. Raw material tank 12 and the below-mentioned small diameter portion 28 are connected through pipe 18. Small diameter portion 28 and reaction product tank 16 are connected through pipe 20. The liquid raw material flowing through pipe 20 passes through the inside of constant temperature bath 14 to be heated to a predetermined temperature.

Microreactor 10 according to the present embodiment is an apparatus capable of heating a liquid raw material to obtain an intended substance. In the present specification, the liquid raw material means a liquid substance to be reacted or a solution containing a substance to be reacted. Microreactor 10 heats a substance to be subjected to reaction to a reaction temperature. Microreactor 10 can obtain an intended substance by heating a substance to be subjected to reaction to cause a reaction.

With respect to raw material tank 12, there is no particular limitation as long as it can store therein a liquid raw material, and it can comprise, for example, a tank made of a metal, a resin, or glass. In the present embodiment, raw material tank 12 comprises a pressure tank made of polyethylene. When raw material tank 12 comprises a pressure tank, the inside of raw material tank 12 can be maintained at a high pressure.

With respect to constant temperature bath 14, there is no particular limitation as long as it can heat a liquid raw material to a predetermined temperature, and it can comprise, for example, a commercially available, known constant temperature bath.

With respect to reaction product tank 16, there is no particular limitation as long as it can store therein a reaction product obtained by heating a liquid raw material, and it can comprise, for example, a tank made of a metal, a resin, or glass.

Microreactor 10 has a not shown nitrogen tank. Nitrogen gas ($N_2$ gas) can be fed from the nitrogen tank into raw material tank 12. The nitrogen tank and raw material tank 12 are connected through nitrogen feed pipe 22. Nitrogen feed pipe 22 is provided with pressure regulating valve 24 (regulator). The pressure of the nitrogen gas in raw material tank 12 can be regulated by pressure regulating valve 24.

Nitrogen gas corresponds to the "gas" in the present invention. The nitrogen tank and nitrogen feed pipe 22 for feeding nitrogen gas correspond to the "gas feeding means" in the present invention. Pressure regulating valve 24 for regulating the pressure of the nitrogen gas filling raw material tank 12 corresponds to the "pressure regulating means" in the present invention. By pressure regulating valve 24, the flow rate of the liquid raw material transferred from raw material tank 12 to constant temperature bath 14 can be regulated. The range of the pressure of the gas fed to raw material tank 12 is from 1 kPa to 200 MPa, preferably from 10 kPa to 15 MPa.

In raw material tank 12 is stored a liquid raw material. The space above the stored liquid raw material is filled with nitrogen gas. The liquid raw material can be transferred from raw material tank 12 to constant temperature bath 14 through pipe 18 using the pressure of the nitrogen gas present above the liquid raw material. In other words, raw material tank 12 can transfer the liquid raw material to the next device using the pressure of the nitrogen gas (gas) filling the raw material tank. Raw material tank 12 and the nitrogen gas filling the raw material tank correspond to the "transfer means" in the present invention.

Pipe 18 which connects raw material tank 12 and small diameter portion 28 comprises, for example, a tube made of PTFE (polytetrafluoroethylene) having an inner diameter of 1.0 mm Pipe 18 is provided with on-off valve 26. On-off valve 26 is a valve for controlling ON/OFF of the liquid raw material flowing through the inside of pipe 18. On-off valve 26 comprises, for example, a solenoid valve. The pressure in pipe 18 which connects raw material tank 12 and small diameter portion 28 preferably is not more than the permissible pressure of on-off valve 26. When on-off valve 26 comprises a solenoid valve, the pressure in pipe 18 which connects raw material tank 12 and small diameter portion 28 is preferably 1.5 MPa or less, more preferably 0.8 MPa or less.

Figure 5:
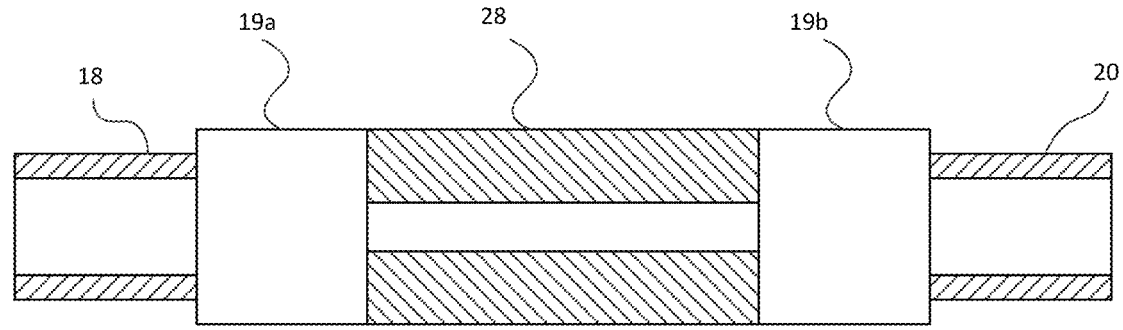
FIG. 5 is an enlarged cross-sectional view of a small diameter portion.

Pipe 18 is provided with small diameter portion 28. Small diameter portion 28 has an inner diameter smaller than the inner diameter of a pipe positioned upstream and/or downstream of the small diameter portion. Small diameter portion 28 may be a tube having an inner diameter smaller than the inner diameter of a pipe positioned upstream and/or downstream of the tube. The inner diameter of small diameter portion 28 is preferably, for example, ϕ0.01 to 0.3 mm Small diameter portion 28 comprises, for example, a tube made of PEEK (polyether ether ketone) having an inner diameter of 0.2 mm. As shown in FIG. 5, pipe 18 and small diameter portion 28 are connected together through connector 19a. Small diameter portion 28 and pipe 20 positioned downstream of the small diameter portion are connected together through connector 19b.

Pipe 20 which connects small diameter portion 28 and reaction product tank 16 comprises, for example, a tube made of PTFE (polytetrafluoroethylene) having an inner diameter of 1.0 mm. The liquid raw material stored in raw material tank 12 is heated to a reaction temperature or higher by constant temperature bath 14, and then transferred to reaction product tank 16 through pipe 20. When the liquid raw material is heated, a substance contained in the liquid raw material undergoes a reaction. An intended substance obtained by the reaction is stored in reaction product tank 16.

The actions and effects of microreactor 10 having the above-mentioned construction according to the first embodiment are descried.

A conventional microreactor has an expensive syringe pump or plunger pump for transferring a liquid raw material. For this reason, there has been a problem in that the production cost for the whole of apparatus is extremely high.

In microreactor 10 according to the present embodiment, a liquid raw material can be transferred using the pressure of nitrogen gas filling raw material tank 12, and hence a syringe pump or a plunger pump is not required. Therefore, the production cost for the whole of apparatus can be drastically reduced.

In microreactor 10 according to the present embodiment, the pressure of the nitrogen gas in raw material tank 12 can be maintained at a constant pressure by pressure regulating valve 24, and therefore it is possible to prevent the flow rate of the liquid raw material flowing through pipe 20 from fluctuating.

Further, pipe 18 which connects raw material tank 12 and pipe 20 is provided with small diameter portion 28. A pressure loss can be controlled by small diameter portion 28. Controlling a pressure loss can regulate the flow rate of the liquid raw material flowing through pipe 18. As a result, the flow rate of the liquid raw material flowing through pipe 20 can be kept constant. Further, a reaction can uniformly proceed, making it possible to stably produce an intended product having consistent quality.

<Second Embodiment>

Hereinbelow, the second embodiment of the present invention will be described in detail with reference to the drawing.

Figure 2:
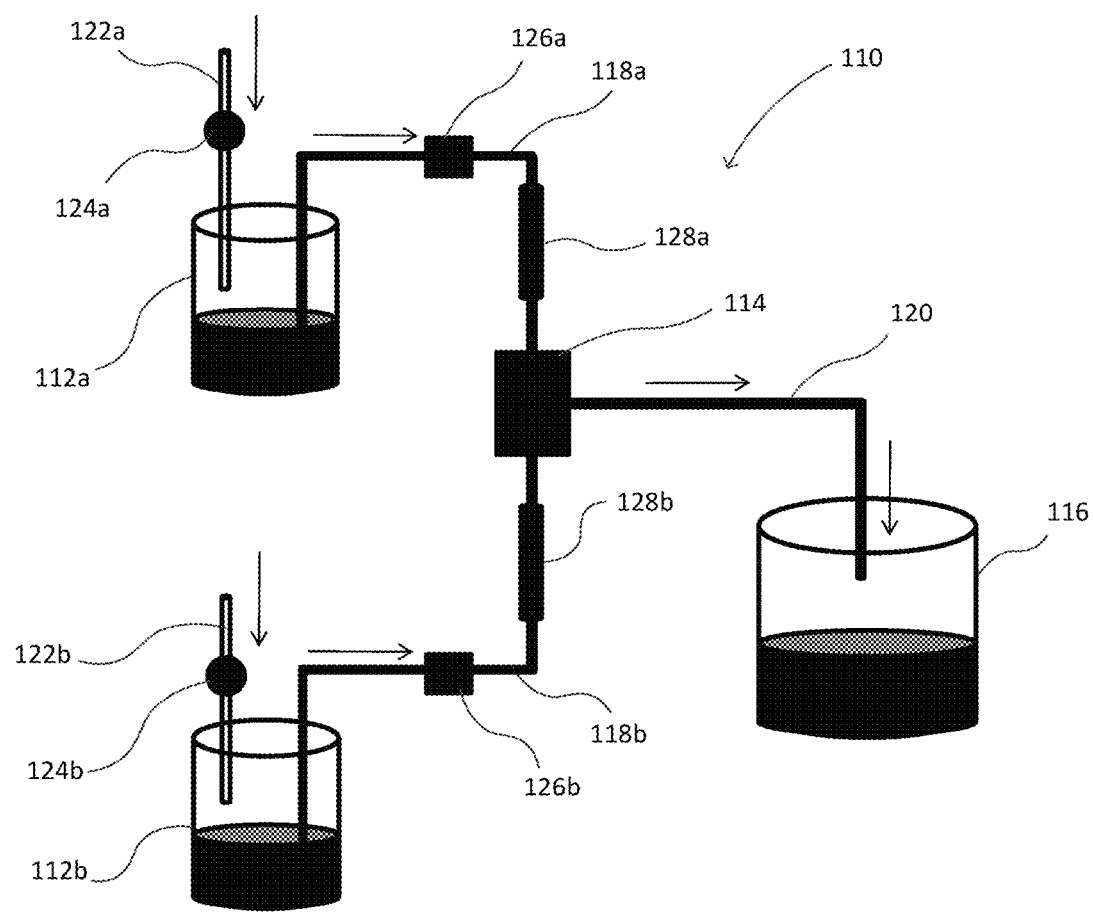
FIG. 2 shows a flow of the microreactor according to the second embodiment.

FIG. 2 shows a flow of the microreactor according to the second embodiment.

As shown in FIG. 2, microreactor 110 according to the second embodiment has two raw material tanks 112a, 112b, mixer 114, and reaction product tank 116. Raw material tanks 112a, 112b are a tank for storing two types of liquid raw materials. The liquid raw materials sent from raw material tanks 112a, 112b are mixed by means of mixer 114. A reaction product obtained by mixing the liquid raw materials is stored in reaction product tank 116. Raw material tank 112a and mixer 114 are connected through pipe 118a. Raw material tank 112b and mixer 114 are connected through pipe 118b. Mixer 114 and reaction product tank 116 are connected through pipe 120.

Microreactor 110 according to the present embodiment is an apparatus capable of mixing two types of liquid raw materials. By mixing two types of liquid raw materials to cause a reaction, an intended reaction product can be obtained.

With respect to raw material tanks 112a, 112b, there is no particular limitation as long as they can store therein a liquid raw material, and they can comprise, for example, a tank made of a metal, a resin, or glass. In the present embodiment, raw material tanks 112a, 112b comprise a pressure tank made of polyethylene. When raw material tanks 112a, 112b comprise a pressure tank, the inside of raw material tanks 112a, 112b can be maintained at a high pressure.

With respect to mixer 114, there is no particular limitation as long as it can mix two types of liquid raw materials with each other, and any mixer can be used. As mixer 114, for example, a commercially available, known micromixer made of a metal, a resin, or glass can be used. The micromixer is a mixer having a microchannel for mixing together a plurality of liquid raw materials. The micromixer can be produced by, for example, forming a microchannel in one surface of a metal plate, and stacking another metal plate on the surface of the metal plate in which the microchannel is formed. With respect to the shape of the microchannel, there is no particular limitation, and, for example, a mixer in which a T-shaped microchannel is formed, or a mixer in which a Y-shaped microchannel is formed can be used. With respect to the width of the microchannel, there is no particular limitation, but, for example, a micromixer in which a microchannel having a width of about 0.01 to 1,000 μm is formed can be used.

With respect to reaction product tank 116, there is no particular limitation as long as it can store therein a reaction product obtained by mixing liquid raw materials, and it can comprise, for example, a tank made of a metal, a resin, or glass.

Microreactor 110 has a not shown nitrogen tank. Nitrogen gas (N$_2$ gas) can be fed from the nitrogen tank into two raw material tanks 112a, 112b. The nitrogen tank and raw material tanks 112a, 112b are connected, respectively, through nitrogen feed pipes 122a, 122b. Nitrogen feed pipes 122a, 122b are provided with pressure regulating valves 124a, 124b (regulators), respectively. The pressures of the nitrogen gas in raw material tanks 112a, 112b can be kept constant, respectively, by pressure regulating valves 124a, 124b. Further, the flow rates of the liquid raw materials transferred from two raw material tanks 112a, 112b to mixer 114 can be regulated, respectively, by pressure regulating valves 124a, 124b. The range of the pressure of the gas fed to raw material tanks 112a, 112b is from 1 kPa to 200 MPa, preferably from 10 kPa to 15 MPa.

Nitrogen gas corresponds to the "gas" in the present invention. The nitrogen tank and nitrogen feed pipes 122a, 122b for feeding nitrogen gas correspond to the "gas feeding means" in the present invention. Pressure regulating valves 124a, 124b for regulating the pressures of nitrogen gas filling raw material tanks 112a, 112b correspond to the "pressure regulating means" in the present invention.

In two raw material tanks 112a, 112b are stored liquid raw materials. The spaces above the stored liquid raw materials are individually filled with nitrogen gas. The liquid raw materials can be transferred from two raw material tanks 112a, 112b to mixer 114 through pipes 118a, 118b using the pressures of the nitrogen gas present above the liquid raw materials. In other words, two raw material tanks 112a, 112b can transfer the liquid raw materials to the next device using the pressures of the nitrogen gas (gas) filling the raw material tanks. Two raw material tanks 112a, 112b and the nitrogen gas filling the respective raw material tanks correspond to the "transfer means" in the present invention.

Pipes 118a, 118b which connect two raw material tanks 112a, 112b and mixer 114 comprise, for example, a tube made of PTFB (polytetrafluoroethylene) having an inner diameter of 1.0 mm Pipes 118a, 118b are provided with on-off valves 126a, 126b, respectively. On-off valves 126a, 126b are a valve for controlling ON/OFF of the liquid raw materials flowing through the inside of pipes 118a, 118b. On-off valves 126a, 126b comprise, for example, a solenoid valve. The pressures in pipes 118a, 118b which connect raw material tanks 112a, 112b and small diameter portions 128a, 128b preferably are not more than the permissible pressures of on-off valves 126a, 126b. When on-off valves 126a, 126b comprise a solenoid valve, the pressures in pipes 118a, 118b which connect raw material tanks 112a, 112b and small diameter portions 128a, 128b are preferably 1.5 MPa or less, more preferably 0.8 MPa or less.

Pipes 118a, 118b which connect two raw material tanks 112a, 112b and mixer 114 are provided with small diameter portions 128a, 128b, respectively. Small diameter portions 128a, 128b may be a tube having an inner diameter smaller than the inner diameter of a pipe positioned upstream and/or downstream of the tube. Small diameter portions 128a, 128b comprise, for example, a tube made of PEEK (polyether ether ketone) having an inner diameter of 0.2 mm Pipes 118a, 118b and small diameter portions 128a, 128b are respectively connected together through not shown connectors.

Pipe 120 which connects mixer 114 and reaction product tank 116 comprises, for example, a tube made of PTFE (polytetrafluoroethylene) having an inner diameter of 1.0 mm. The liquid raw materials stored in two raw material tanks 112a, 112b are mixed together by mixer 114, and then transferred to reaction product tank 116 through pipe 120. Thus, an intended substance obtained by the reaction of substances contained in the two types of liquid raw materials is stored in reaction product tank 116.

The actions and effects of microreactor 110 having the above-mentioned construction according to the second embodiment are descried.

A conventional microreactor has an expensive syringe pump or plunger pump for transferring a liquid raw material. For this reason, there has been a problem in that the production cost for the whole of apparatus is extremely high.

In microreactor 110 according to the present embodiment, liquid raw materials can be transferred using the pressures of nitrogen gas filling raw material tanks 112a, 112b, and hence a syringe pump or a plunger pump is not required. Therefore, the production cost for the whole of apparatus can be drastically reduced.

In microreactor 110 according to the present embodiment, the pressures of the nitrogen gas in two raw material tanks 112a, 112b can be maintained at a constant pressure by pressure regulating valves 124a, 124b, and therefore it is possible to prevent the flow rates of the liquid raw materials transferred to mixer 114 from fluctuating.

Further, pipes 118a, 118b which connect two raw material tanks 112a, 112b and mixer 114 are provided with small diameter portions 128a, 128b, respectively. A pressure loss can be controlled by small diameter portions 128a, 128b. Controlling a pressure loss can regulate the flow rates of the liquid raw materials flowing through pipes 118a, 118b. Further, it is possible to prevent the liquid raw materials from flowing back into raw material tanks 112a, 112b. As a result, the flow rates of the liquid raw materials fed to mixer 114 can be controlled to be constant. Further, a reaction can uniformly proceed, making it possible to stably produce an intended product having consistent quality.

Furthermore, in microreactor 110 according to the present embodiment, the ratio of the flow rates of the liquid raw materials transferred from two raw material tanks 112a, 112b to mixer 114 can be controlled to be constant. For example, when a difference is caused between the pressures of nitrogen gas sealed in two raw material tanks 112a, 112b, a backflow is likely to occur from the raw material tank having a higher pressure toward the raw material tank having a lower pressure. In microreactor 110 according to the present embodiment, a pressure loss is controlled by small diameter portions 128a, 128b, and therefore the flow rates of the liquid raw materials become small. As a result, the occurrence of a backflow of the liquid raw materials is prevented, so that the ratio of the flow rates of the two types of liquid raw materials fed to mixer 114 is kept constant.

Thus, in microreactor 110 according to the present embodiment, pipes 118a, 118b which connect the raw material tanks and the mixer are provided with small diameter portions 128a, 128b, respectively, and the ratio of the flow rates of the two types of liquid raw materials fed to mixer 114 is kept constant.

Microreactor 110 according to the present embodiment can transfer liquid raw materials using the gas pressures in raw material tanks. Further, microreactor 110 according to the present embodiment has small diameter portions 128a, 128b, and hence can stably transfer the liquid raw materials using the gas pressures. Microreactor 110 according to the present embodiment is extremely unique in that these advantages have been able to be achieved, and thus is an epoch-making invention.

<Third Embodiment>

Hereinbelow, the third embodiment of the present invention will be described in detail with reference to the drawing.

The third embodiment is substantially the same as the above-descried second embodiment except that three types of liquid raw materials are reacted in two stages. In the following description, with respect to like parts or portions in the present embodiment and the second embodiment, the description is frequently omitted.

Figure 3:
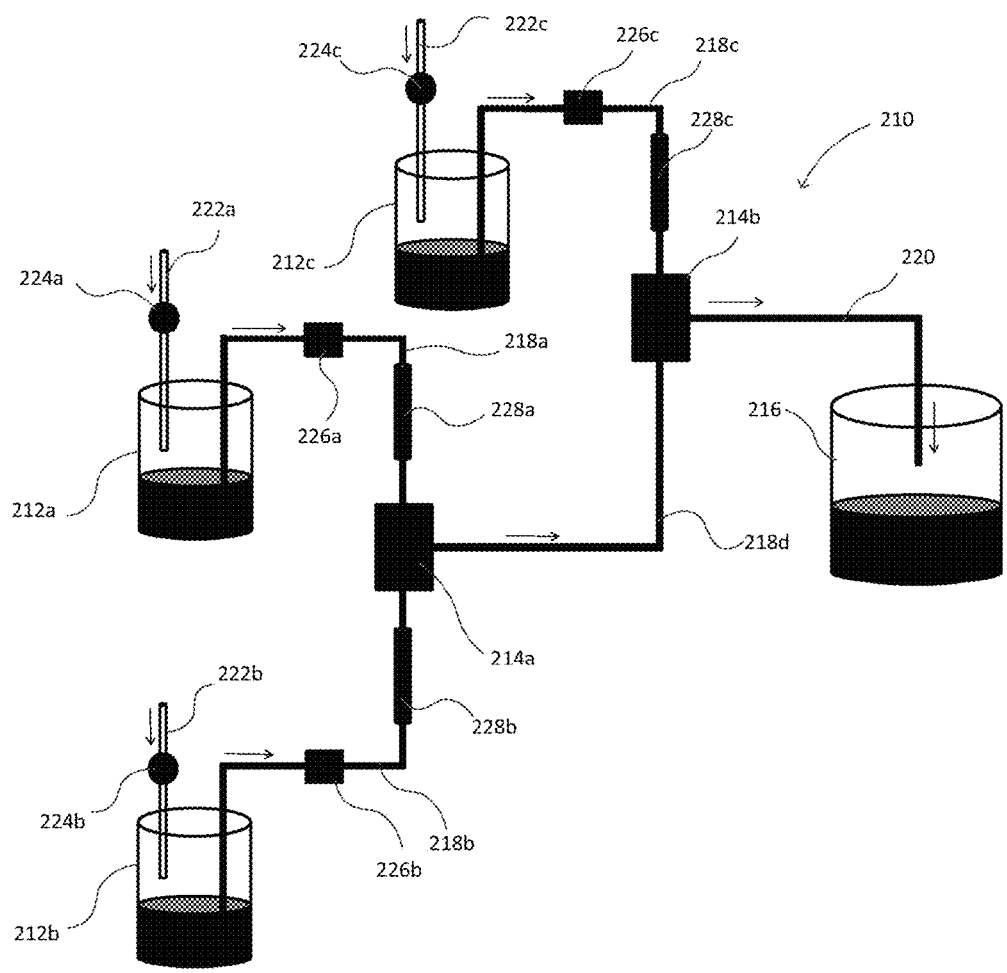
FIG. 3 shows a flow of the microreactor according to the third embodiment.

FIG. 3 shows a flow of the microreactor according to the third embodiment of the present invention.

As shown in FIG. 3, microreactor 210 according to the present embodiment has three raw material tanks 212a, 212b, 212c, two mixers 214a, 214b, and reaction product tank 216. Raw material tanks 212a, 212b, 212c are a tank for storing three types of liquid raw materials. The liquid raw materials sent from raw material tanks 212a, 212b, 212c are mixed by means of two mixers 214a, 214b. A reaction product obtained by mixing the three types of liquid raw materials is stored in reaction product tank 216. Raw material tank 212a and mixer 214a are connected through pipe 218a. Raw material tank 212b and mixer 214a are connected through pipe 218b. Raw material tank 212c and mixer 214b are connected through pipe 218c. Mixer 214a and mixer 214b are connected through pipe 218d. Mixer 214b and reaction product tank 216 are connected through pipe 220.

Microreactor 210 according to the present embodiment is an apparatus capable of mixing three types of liquid raw materials in two stages.

First, the liquid raw material sent from first raw material tank 212a and the liquid raw material sent from second raw material tank 212b are mixed by means of first mixer 214a. Then, the two types of liquid raw materials mixed by first mixer 214a and the liquid raw material sent from third raw material tank 212c are mixed by means of second mixer 214b. Thus, the three types of liquid raw materials can be mixed in two stages to cause a reaction.

Microreactor 210 has a not shown nitrogen tank. Nitrogen gas ($N_2$ gas) can be fed from the nitrogen tank into three raw material tanks 212a, 212b, 212c. The nitrogen tank and raw material tanks 212a, 212b, 212c are connected, respectively, through nitrogen feed pipes 222a, 222b, 222c. Nitrogen feed pipes 222a, 222b, 222c are provided with pressure regulating valves 224a, 224b, 224c (regulators), respectively. The pressures of the nitrogen gas in raw material tanks 212a, 212b, 212c can be kept constant, respectively, by pressure regulating valves 224a, 224b, 224c. Further, the flow rates of the liquid raw materials transferred from three raw material tanks 212a, 212b, 212c to mixers 214a, 214b can be regulated, respectively, by pressure regulating valves 224a, 224b, 224c. The range of the pressure of the gas fed to raw material tanks 212a, 212b, 212c is from 1 kPa to 200 MPa, preferably from 10 kPa to 15 MPa.

Nitrogen gas corresponds to the "gas" in the present invention. The nitrogen tank and nitrogen feed pipes 222a, 222b, 222c for feeding nitrogen gas correspond to the "gas feeding means" in the present invention. Pressure regulating valves 224a, 224b, 224c for regulating the pressures of the nitrogen gas filling raw material tanks 212a, 212b, 212c correspond to the "pressure regulating means" in the present invention.

In three raw material tanks 212a, 212b, 212c are stored liquid raw materials. The spaces above the stored liquid raw materials are individually filled with nitrogen gas. The liquid raw materials can be transferred to the next device using the pressures of the nitrogen gas present above the liquid raw materials. Specifically, the liquid raw material stored in first raw material tank 212a can be transferred to first mixer 214a. The liquid raw material stored in second raw material tank 212b can be transferred to first mixer 214a. The liquid raw material stored in third raw material tank 212c can be transferred to second mixer 214b. Three raw material tanks 212a, 212b, 212c and the nitrogen gas filling the respective raw material tanks correspond to the "transfer means" in the present invention.

Pipes 218a, 218b, 218c which connect the raw material tanks and the mixers comprise, for example, a tube made of PTFE (polytetrafluoroethylene) having an inner diameter of 1.0 mm Pipes 218a, 218b, 218c are provided with on-off valves 226a, 226b, 226c, respectively. On-off valves 226a, 226b, 226c are a valve for controlling ON/OFF of the liquid raw materials flowing through the inside of pipes 218a, 218b, 218c. On-off valves 226a, 226b, 226c comprise, for example, a solenoid valve. The pressures in pipes 218a, 218b, 218c which connect raw material tanks 212a, 212b, 212c and small diameter portions 228a, 228b, 228c preferably are not more than the permissible pressures of on-off valves 226a, 226b, 226c. When on-off valves 226a, 226b, 226c comprise a solenoid valve, the pressures in pipes 218a, 218b, 218c which connect raw material tanks 212a, 212b, 212c and small diameter portions 228a, 228b, 228c are preferably 1.5 MPa or less, more preferably 0.8 MPa or less.

Pipes 218a, 218b, 218c which connect the raw material tanks and the mixers are provided with small diameter portions 228a, 228b, 228c, respectively. Small diameter portions 228a, 228b, 228c may be a tube having an inner diameter smaller than the inner diameter of a pipe positioned upstream and/or downstream of the tube. Small diameter portions 228a, 228b, 228c comprise, for example, a tube made of PEEK (polyether ether ketone) having an inner diameter of 0.2 mm Pipes 218a, 218b, 218c and small diameter portions 228a, 228b, 228c are respectively connected together through not shown connectors.

Pipe 220 which connects mixer 214b and reaction product tank 216 comprises, for example, a tube made of PTFE (polytetrafluoroethylene) having an inner diameter of 1.0 mm. The liquid raw materials stored in three raw material tanks 212a, 212b, 212c are mixed by mixers 214a, 214b in two stages, and then transferred to reaction product tank 216 through pipe 220. Thus, an intended substance obtained by the reaction of substances contained in the three types of liquid raw materials is stored in reaction product tank 216.

The actions and effects of microreactor 210 having the above-mentioned construction according to the third embodiment are descried.

A conventional microreactor has an expensive syringe pump or plunger pump for transferring a liquid raw material. For this reason, there has been a problem in that the production cost for the whole of apparatus is extremely high.

In microreactor 210 according to the present embodiment, liquid raw materials can be transferred using the pressures of nitrogen gas filling raw material tanks 212a, 212b, 212c, and hence a syringe pump or a plunger pump is not required. Therefore, the production cost for the whole of apparatus can be drastically reduced.

In microreactor 210 according to the present embodiment, the pressures of the nitrogen gas in three raw material tanks 212a, 212b, 212c can be maintained at a constant pressure by pressure regulating valves 224a, 224b, 224c, and therefore it is possible to prevent the flow rates of the liquid raw materials transferred to mixers 214a, 214b from fluctuating.

Further, pipes 218a, 218b, 218c which connect raw material tanks 212a, 212b, 212c and mixers 214a, 214b are provided with small diameter portions 228a, 228b, 228c, respectively. A pressure loss can be controlled by small diameter portions 228a, 228b, 228c. Controlling a pressure loss can regulate the flow rates of the liquid raw materials flowing through pipes 218a, 218b, 218c. Further, it is possible to prevent the liquid raw materials from flowing back into raw material tanks 212a, 212b, 212c. As a result, the flow rates of the liquid raw materials fed to mixers 214a, 214b can be controlled to be constant. Further, a reaction can uniformly proceed, making it possible to stably produce an intended product having consistent quality.

Furthermore, in microreactor 210 according to the present embodiment, the ratio of the flow rates of the liquid raw materials transferred from two raw material tanks 212a, 212b to mixer 214a can be controlled to be constant. For example, when a difference is caused between the pressures of nitrogen gas sealed in two raw material tanks 212a, 212b, a backflow is likely to occur from the raw material tank having a higher pressure toward the raw material tank having a lower pressure. In microreactor 210 according to the present embodiment, a pressure loss is controlled by small diameter portions 228a, 228b, and therefore the flow rates of the liquid raw materials become small. As a result, the occurrence of a backflow of the liquid raw materials is prevented, so that the ratio of the flow rates of the two types of liquid raw materials fed to mixer 214a is kept constant. Similarly, in second mixer 214b, the ratio of the flow rates of the liquid raw materials transferred from raw material tank 212c and mixer 214a is kept constant.

Thus, in microreactor 210 according to the present embodiment, pipes 218a, 218b, 218c which connect the raw material tanks and the mixers are provided with small diameter portions 228a, 228b, 228c, respectively, and the ratio of the flow rates of the three types of liquid raw materials fed to mixers 214a, 214b is kept constant.

Microreactor 210 according to the present embodiment can transfer liquid raw materials using the gas pressures in raw material tanks. Further, microreactor 210 according to the present embodiment has small diameter portions 228a, 228b, 228c, and hence can stably transfer the liquid raw materials using the gas pressures. Microreactor 210 according to the present embodiment is extremely unique in that these advantages have been able to be achieved, and thus is an epoch-making invention.

<Fourth Embodiment>

Hereinbelow, the fourth embodiment of the present invention will be described in detail with reference to the drawing.

The fourth embodiment is substantially the same as the above-descried second embodiment except that two types of liquid raw materials are not mixed but a liquid raw material and a gas raw material are mixed with each other. In the following description, with respect to like parts or portions in the present embodiment and the second embodiment, the description is frequently omitted.

Figure 4:
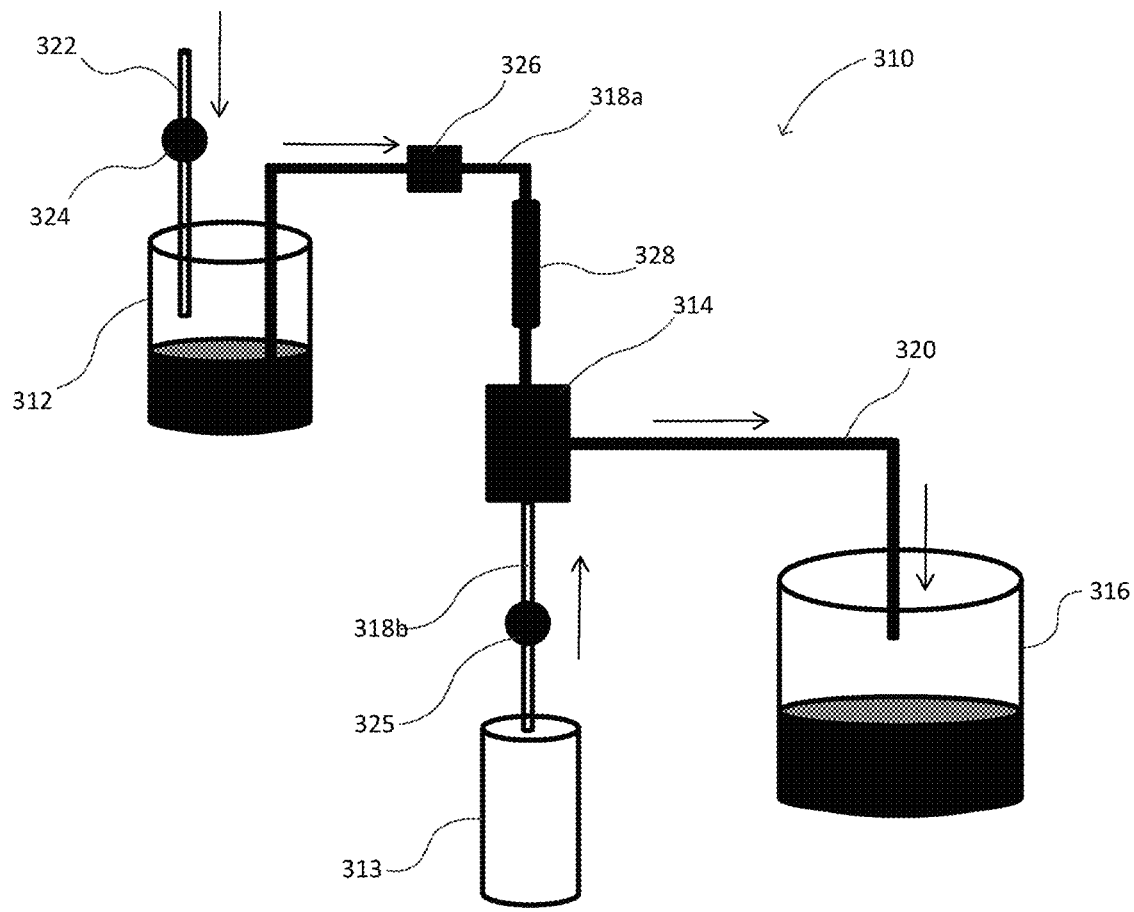
FIG. 4 shows a flow of the microreactor according to the fourth embodiment.

FIG. 4 shows a flow of the microreactor according to the fourth embodiment of the present invention.

As shown in FIG. 4, microreactor 310 according to the present embodiment has raw material tank 312, raw material tank 313, mixer 314, and reaction product tank 316. Raw material tank 312 is a tank for storing a liquid raw material. Raw material tank 313 is a tank for storing a gas raw material. The liquid raw material and the gas raw material are mixed by means of mixer 314. A reaction product obtained by mixing the liquid raw material and the gas raw material is stored in reaction product tank 316. Raw material tank 312 and mixer 314 are connected through pipe 318a. Raw material tank 313 and mixer 314 are connected through pipe 318b. Mixer 314 and reaction product tank 316 are connected through pipe 320.

Microreactor 310 according to the present embodiment is an apparatus capable of mixing a liquid raw material and a gas raw material to obtain a reaction product.

Microreactor 310 has a not shown nitrogen tank. Nitrogen gas ($N_2$ gas) can be fed from the nitrogen tank into raw material tank 312. The nitrogen tank and raw material tank 312 are connected through nitrogen feed pipe 322. Nitrogen feed pipe 322 is provided with pressure regulating valve 324 (regulator). The pressure of the nitrogen gas in raw material tank 312 can be kept constant by pressure regulating valve 324. Further, the flow rate of the liquid raw material transferred from raw material tank 312 to mixer 314 can be regulated by pressure regulating valve 324. The range of the pressure of the gas fed to raw material tank 312 is from 1 kPa to 200 MPa, preferably from 10 kPa to 15 MPa.

Nitrogen gas corresponds to the "gas" in the present invention. The nitrogen tank and nitrogen feed pipe 322 for feeding nitrogen gas correspond to the "gas feeding means" in the present invention. Pressure regulating valve 324 for regulating the pressure of the nitrogen gas filling raw material tank 312 corresponds to the "pressure regulating means" in the present invention.

In raw material tank 312 is stored a liquid raw material. The space above the stored liquid raw material is filled with nitrogen gas. The liquid raw material stored in raw material tank 312 can be transferred to mixer 314 using the pressure of the nitrogen gas present above the liquid raw material. Raw material tank 312 and the nitrogen gas filling the raw material tank correspond to the "transfer means" in the present invention.

Pipe 318a which connects raw material tank 312 and mixer 314 is provided with small diameter portion 328. Small diameter portion 328 may be a tube having an inner diameter smaller than the inner diameter of a pipe positioned upstream and/or downstream of the tube. Small diameter portion 328 comprises, for example, a tube made of PEEK (polyether ether ketone) having an inner diameter of 0.2 mm Pipe 318a and small diameter portion 328 are connected together through a not shown connector.

Pipe 318b which connects raw material tank 313 and mixer 314 is provided with pressure regulating valve 325 (regulator). The pressure of the gas raw material fed to mixer 314 from raw material tank 313 can be regulated by pressure regulating valve 325. Further, the flow rate of the gas raw material fed to mixer 314 can be kept constant by pressure regulating valve 325.

By microreactor 310 according to the fourth embodiment, the same effects as those obtained by microreactor 110 according to the second embodiment can be obtained.

The microreactor of the present invention can be applied not only to a reaction system in which two types of liquid raw materials are mixed but also to a reaction system in which a liquid raw material and a gas raw material are mixed.

<Other Embodiments>

(1) In the above-mentioned embodiments, an example in which the number of the raw material tanks is 1, 2, or 3 was shown, but the number of the raw material tanks is not limited to these numbers.

(2) In the above-mentioned embodiments, an example in which the material for the pipe is a resin was shown, but the material for the pipe is not limited to this. The pipe may be formed from, for example, a metal.

(3) In the above-mentioned embodiments, an example in which the small diameter portion is a tube made of a resin was shown, but the small diameter portion is not limited to this. The small diameter portion may be formed from, for example, a tube of a metal. Alternatively, a known back pressure tube or back pressure regulator used for regulating a back pressure in HPLC or ion chromatography may be used as the small diameter portion.

(4) In the above-mentioned embodiments, an example in which the gas for transferring a liquid raw material is nitrogen was shown, but the type of the gas is not limited to this. The gas for transferring a liquid raw material may be, for example, air or argon gas.

(5) In the above-mentioned embodiments, an example in which the substance to be reacted (liquid raw material and/or a solution of the raw material) is transferred was shown, but, for example, a solvent for diluting the raw material, a reaction terminator, or a solvent for extraction may be transferred.

In the above-mentioned embodiments, an example in which a raw material tank and a small diameter portion are connected through one pipe was shown, but the pipe connected to a raw material tank may be branched into two or more pipes. That is, a plurality of pipes are branched from a raw material tank, and a small diameter portion may be connected to each of the branched pipes.

The small diameter portion has an inner diameter smaller than the inner diameter of a pipe positioned upstream and/or downstream of the small diameter portion. The small diameter portion preferably has an inner diameter smaller than the inner diameters of pipes positioned upstream and downstream of the small diameter portion. The small diameter portion is described below in more detail.

The small diameter portion may comprise a valve. For example, a valve having a valve body or a spool capable of controlling the size of a channel can be used as the small diameter portion. For example, a gate valve or a globe valve can be used as the small diameter portion. For example, a "2-way valve" capable of controlling the size of a channel (manufactured by GL Science Inc.) can be used as the small diameter portion.

The small diameter portion may comprise an orifice. For example, an orifice having a thin plate made of a resin or a metal in which an opening smaller than the inner diameters of pipes positioned upstream and downstream of the orifice may be used as the small diameter portion. The orifice may be an orifice having one opening formed in one plate, or an orifice having a plurality of openings formed in one plate. For example, an in-line filter for HPLC or ion chromatography can be used as the small diameter portion. For example, a PEEK pre-column filter for HPLC (manufactured by Shimadzu GLC Ltd.) can be used as the small diameter portion.

Figure 6:
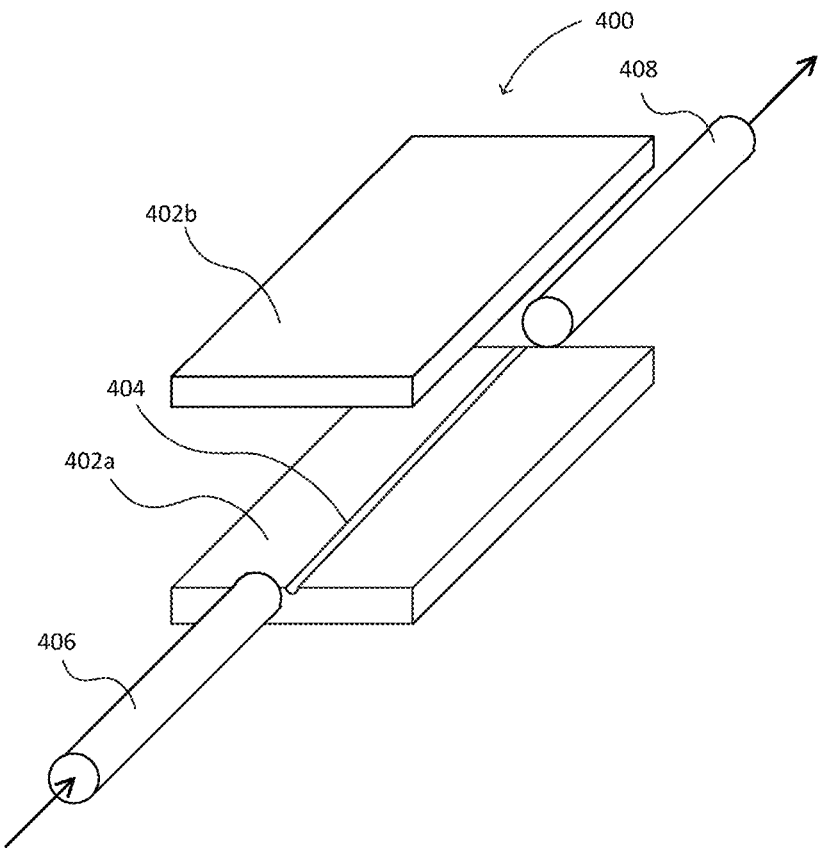
FIG. 6 shows another example of the small diameter portion.

As shown in FIG. 6, small diameter portion 400 can be produced by forming microchannel 404 in one surface of metal plate 402a, and stacking another metal plate 402b on the surface of metal plate 402a in which microchannel 404 is formed. That is, small diameter portion 400 may be metal plate 402a having microchannel 404 formed thereon, like the above-mentioned micromixer. Microchannel 404 has an inner diameter smaller than the inner diameters of pipe 406 positioned upstream of small diameter portion 400 and pipe 408 positioned downstream of small diameter portion 400.

Figure 7:
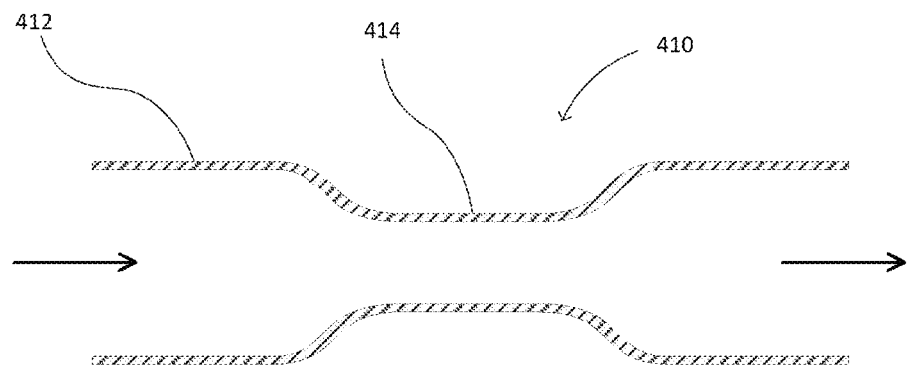
FIG. 7 shows further another example of the small diameter portion.

As shown in FIG. 7, small diameter portion 410 may be tube 412 made of a metal or a resin, which is physically deformed so that the inner diameter of tube 412 is partially reduced. Inner diameter 414 of tube 412 at the deformed portion has an inner diameter smaller than the inner diameter of a pipe positioned upstream and/or downstream of the tube.

Hereinbelow, more specific Examples of the present invention will be described.

EXAMPLE 1

Microreactor 10 described above in connection with the embodiment 1 was applied to a Diels-Alder reaction shown in the following formula (1).

[Chemical formula 1]

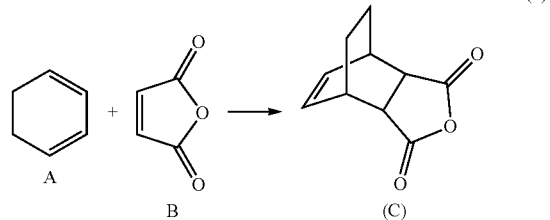

(1)

9.8 g (10 mmol) of maleic anhydride (A) and 8.0 g (10 mmol) of 1,3-cyclohexadiene (B) were dissolved in 100 ml of toluene to obtain a liquid raw material. The obtained liquid raw material was stored in a raw material tank.

The liquid raw material stored in the raw material tank was transferred to a constant temperature bath using the pressure of nitrogen gas filling the raw material tank. In this instance, the pressure of the nitrogen gas in the raw material tank was controlled to be 0.02 MPa. A pipe running through the raw material tank and the constant temperature bath was provided with a tube having an inner diameter of 0.2 mm and a length of 15 cm as a small diameter portion. The pipe running through the constant temperature bath has an inner diameter of 1.0 mm and a length of 4 m. The temperature set at the constant temperature bath is 80° C.

By transferring the liquid raw material to the constant temperature bath at a constant flow rate, a Diels-Alder addition product (C) was able to be quantitatively obtained.

EXAMPLE 2

Microreactor 110 described above in connection with the embodiment 2 was applied to a bromination reaction for carbazole shown in the following formula (2).

[Chemical formula 2]

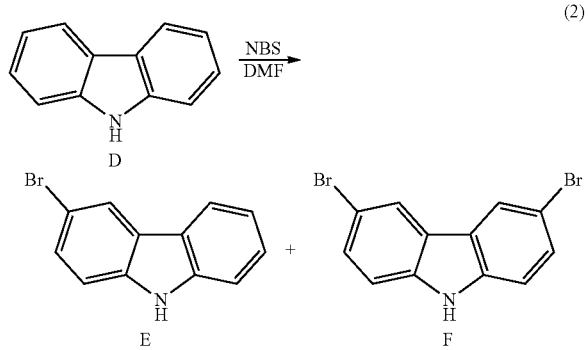

(2)

25 g (0.15 mol) of carbazole (D) was dissolved in DMF to obtain 250 ml of a liquid raw material. The obtained liquid raw material was stored in a first raw material tank.

26.6 g (0.15 mol) of N-bromosuccinimide (NBS) was dissolved in DMF to obtain 250 ml of a liquid raw material. The obtained liquid raw material was stored in a second raw material tank.

The liquid raw materials stored in the raw material tanks were transferred to a mixer using the pressures of nitrogen gas filling the raw material tanks. In this instance, the pressure of the nitrogen gas in the first raw material tank was controlled to be 0.14 MPa. The pressure of the nitrogen gas in the second raw material tank was controlled to be 0.03 MPa.

Using a mixer in which a T-shaped microchannel having an inner diameter of 1.0 mm is formed (YMC-P-0020, manufactured by YMC Co., Ltd.), the two types of liquid raw materials were mixed. A pipe which connects the first raw material tank and the mixer was provided with a tube having an inner diameter of 0.2 mm and a length of 5 cm as a small diameter portion.

The mixer and a reaction product tank are connected through a pipe having an inner diameter of 1.0 mm and a length of 1 m and having the outer surface cooled to −5° C. By allowing the two types of liquid raw materials mixed by the mixer to flow through this pipe, a bromination reaction proceeded, so that bromocarbazole (E) was obtained at a reaction conversion of 80%. In this instance, a dibromocarbazole (F) was formed in an amount of 7%.

EXAMPLE 3

Microreactor 110 described above in connection with the embodiment 2 was applied to a synthesis reaction of sodium styrenesulfonate (PSSNa)(H) shown in the following formula (3).

[Chemical formula 3]

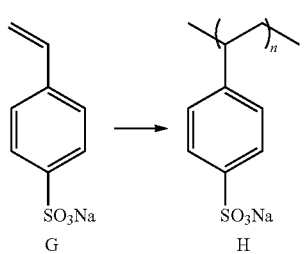

(3)

50 g of a sodium styrenesulfonate monomer (G) was dissolved in water to obtain 250 ml of a liquid raw material. The obtained liquid raw material was stored in a first raw material tank.

0.5 g of sodium persulfate was dissolved in water to obtain 250 ml of a liquid raw material. The obtained liquid raw material was stored in a second raw material tank.

The liquid raw materials stored in the raw material tanks were transferred to a mixer using the pressures of nitrogen gas filling the raw material tanks. In this instance, the pressure of the nitrogen gas in the first raw material tank was controlled to be 0.03 MPa. The pressure of the nitrogen gas in the second raw material tank was controlled to be 0.03 MPa.

Using a mixer in which a T-shaped microchannel having an inner diameter of 1.0 mm is formed (YMC-P-0020, manufactured by YMC Co., Ltd.), the two types of liquid raw materials were mixed. Pipes which connect the two raw material tanks and the mixer were individually provided with a tube having an inner diameter of 0.2 mm and a length of 10 cm as a small diameter portion.

The mixer and a reaction product tank are connected through a pipe having an inner diameter of 1.0 mm and a length of 10 m and having the outer surface heated to 80° C. By allowing the two types of liquid raw materials mixed by the mixer to flow through this pipe, sodium polystyrenesulfonate (H) (Mn: 83,191; Mw: 148,234; Mw/Mn: 1.78) was obtained as a reaction product.

The microreactor was continuously operated for 18 hours. As a result, the liquid raw materials could be stably transferred. Further, the reaction product could be stably produced.

EXAMPLE 4

Microreactor 210 described above in connection with the embodiment 3 was applied to a synthesis reaction of naphthylboronic acid shown in the following formula (4).

[Chemical formula 4]

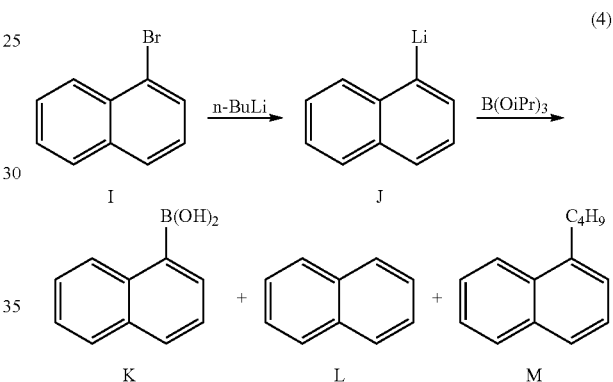

(4)

6.3 g of 1-bromonaphthalene (I) was dissolved in THF to obtain 100 ml (0.31 M) of a liquid raw material. The obtained liquid raw material was stored in a first raw material tank.

25 ml of a 1.6 M n-BuLi hexane solution was diluted with 75 ml of cyclopentyl methyl ether (CPME) to obtain 100 ml (0.4 M) of a liquid raw material. The obtained liquid raw material was stored in a second raw material tank.

11.6 g of triisopropyl borate (B(OiPr)$_3$) was dissolved in THF to obtain 100 ml (0.62 M) of a liquid raw material. The obtained liquid raw material was stored in a third raw material tank.

The liquid raw materials stored in the first and second raw material tanks were transferred to a first mixer using the pressures of nitrogen gas filling the raw material tanks. In this instance, the pressure of the nitrogen gas in the first raw material tank was controlled to be 0.07 MPa. The pressure of the nitrogen gas in the second raw material tank was controlled to be 0.07 MPa. The two types of liquid raw materials were mixed using the first mixer at room temperature to cause a lithiation in a pipe having an inner diameter of 1.0 mm and a length of 20 cm.

The liquid raw material stored in the third raw material tank was transferred to a second mixer using the pressure of nitrogen gas filling the raw material tank. In this instance, the pressure of the nitrogen gas in the third raw material tank was controlled to be 0.07 MPa.

Using a mixer in which a T-shaped microchannel having an inner diameter of 1.0 mm is formed (YMC-P-0020, manufactured by YMC Co., Ltd.), the liquid raw materials were mixed. Pipes which connect the raw material tanks and the mixers were individually provided with a tube having an inner diameter of 0.2 mm and a length of 5 cm as a small diameter portion.

The two types of liquid raw materials mixed by the first mixer and the liquid raw material stored in the third raw material tank were mixed by the second mixer to effect a reaction in a pipe having an inner diameter of 1 mm and a length of 100 cm. As a result, 1-naphthylboronic acid (K) which is an intended reaction product was obtained.

The results of an analysis by HPLC made with respect to the obtained reaction product showed that 1-naphthylboronic acid (K) was 92%, 1-bromonaphthalene (I) was 0.4%, and naphthalene (L) which is a debromination product was 4%. The formation of a butyl addition product (M), which is likely to be formed under high temperature conditions, was not confirmed.

EXAMPLE 5

Figure 8:
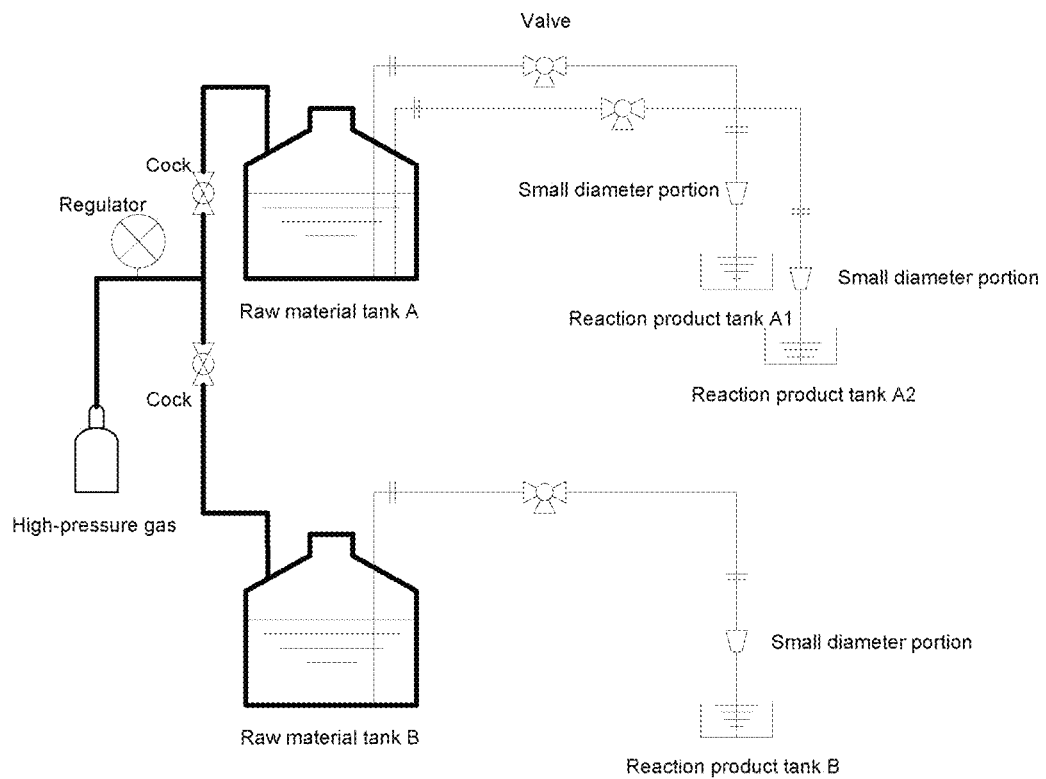
FIG. 8 shows a flow of the microreactor in Example 5.

An apparatus shown in FIG. 8 was assembled using two raw material tanks. Using the assembled apparatus, numbering-up for three channels was studied.

As shown in FIG. 8, nitrogen gas was fed from the common nitrogen gas feed source into raw material tank A and raw material tank B. A pipe on the outlet side of the nitrogen gas feed source was provided with a pressure regulating valve (regulator). The end of the pressure regulating valve was branched, and a cock and a raw material tank were connected to each of the resultant branches.

To raw material tank A were connected two ⅛-inch tubes made of PTFE having an inner diameter of 1.58 mm and a length of 1,300 mm (tube having 800-mm and 500-mm tubes connected). These tubes are referred to as "channel A1" and "channel A2".

To raw material tank B was connected one PTFE tube which is the same as mentioned above. This tube is referred to as "channel B".

To the end of each tube were connected a three-way valve, a drain, and a 1/16-inch tube made of PTFE having an inner diameter of 1 mm and a length of 300 mm. To the end of the tube was connected a 1/16-inch tube made of PEEK having an inner diameter of 0.25 mm and a length of 80 mm. This PEEK tube corresponds to the small diameter portion in the present invention. To the end of the small diameter portion was connected a reaction product tank.

Water was placed in each raw material tank. The pressure of the gas fed to the raw material tank was set to 50 kPa. The valve of channel A2 was opened 30 seconds after the valve of channel A1 was opened. The valve of channel B was opened 30 seconds after the valve of channel A2 was opened. The valves were closed 10 minutes respectively after the valves were opened. After the valves were closed, weights of the reaction product tanks were measured. From the measured weights of the reaction product tanks, a flow rate of each channel was determined. In accordance with the above procedure, the measurement of a flow rate was performed three times. The results of the measurement are shown in Table 1 below.

TABLE 1

| | Channel A1 (ml/min) | Channel A2 (ml/min) | Channel B (ml/min) | Average for three channels (ml/min) | Standard deviation (ml/min) | RSD (%) |
| --- | --- | --- | --- | --- | --- | --- |
| Run1 | 2.793 | 2.758 | 2.745 | 2.765 | 0.009 | 0.33 |
| Run2 | 2.801 | 2.765 | 2.745 | 2.770 | 0.014 | 0.51 |
| Run3 | 2.798 | 2.748 | 2.731 | 2.759 | 0.012 | 0.44 |

When a comparison was made between the flow rates of the three channels, an RSD (relative standard deviation) which is an index of dispersion was about 0.5%, which indicates that the dispersion of the flow rates was small. As apparent from the above, in the microreactor of the present invention, a liquid can be allowed to flow almost evenly into a plurality of channels from a raw material tank.

By the microreactor of the present invention, not only can numbering-up be achieved by arranging the apparatuses in parallel, but also numbering-up can be achieved by connecting a plurality of channels to one raw material tank.

Two channels are connected to raw material tank A, and one channel is connected to raw material tank B. Although the number of the channels connected to raw material tank A and the number of the channel connected to raw material tank B are different from each other, these channels have the same flow rate. From this, it is apparent that the microreactor of the present invention can allow a liquid to flow almost evenly into a plurality of channels. Such a characteristic effect can be obtained by using the small diameter portion. In contrast, when using a conventional syringe pump or plunger pump, the flow rate of channel A1 and channel A2 is about half of the flow rate of channel B.

EXAMPLE 6

Figure 9:
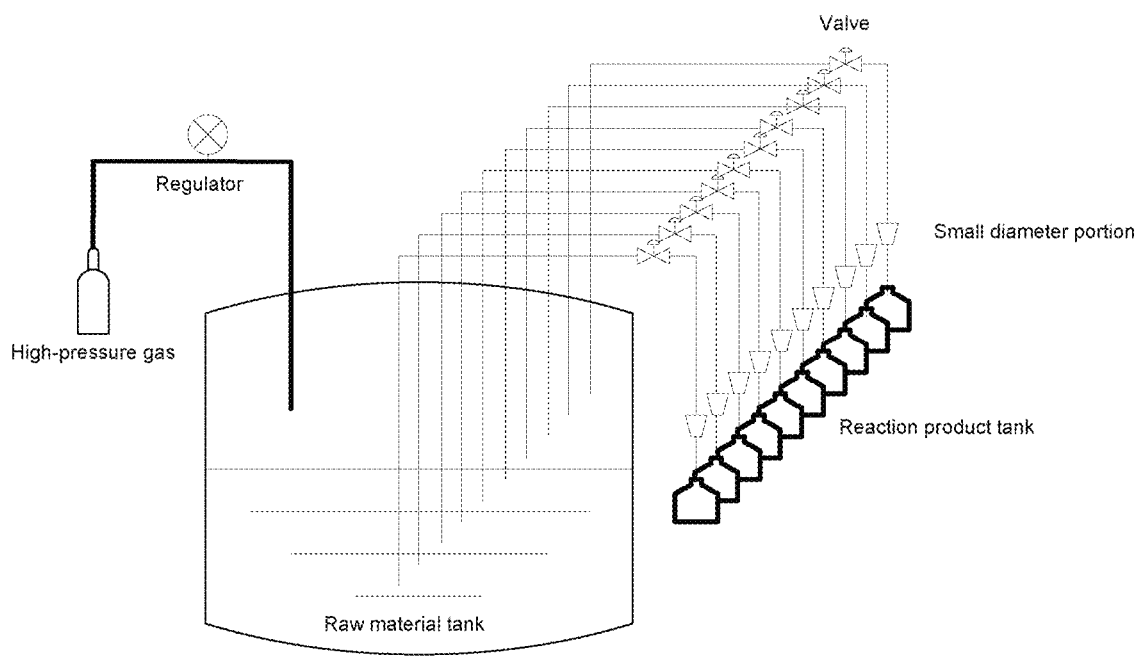
FIG. 9 shows a flow of the microreactor in Example 6.

Ten channels were connected to one raw material tank to assemble an apparatus shown in FIG. 9. Using the assembled apparatus, numbering-up for ten channels was studied.

As shown in FIG. 9, high-pressure nitrogen gas was fed from a nitrogen gas feed source to a raw material tank. To the raw material tank were connected ten ⅛-inch tubes made of PTFE having an inner diameter of 1.58 mm and a length of 1,300 mm (tube having 800-mm and 500-mm tubes connected). To the end of each tube were connected a three-way valve and a 1/16-inch tube made of PTFE having an inner diameter of 1 mm and a length of 300 mm. To the end of the tube was connected a tube made of PEEK having an inner diameter of 0.25 mm and a length of 200 mm. This PEEK tube corresponds to the small diameter portion in the present invention. To the end of the small diameter portion was connected a reaction product tank.

Water was placed in the raw material tank. The pressure of the gas fed to the raw material tank was set to 0.1 MPa. The valves respectively attached to the ten channels were successively opened every 5 seconds. The valves were closed 10 minutes respectively after the valves were opened. After the valves were closed, weights of the reaction product tanks were measured. From the measured weights of the reaction product tanks, a flow rate of each channel was determined. In accordance with the above procedure, the measurement of a flow rate was performed three times. The results of the measurement are shown in Tables 2 and 3 below.

TABLE 2

| | Channel 1 (ml/min) | Channel 2 (ml/min) | Channel 3 (ml/min) | Channel 4 (ml/min) | Channel 5 (ml/min) | Channel 6 (ml/min) | Channel 7 (ml/min) | Channel 8 (ml/min) | Channel 9 (ml/min) | Channel 10 (ml/min) |
|---|---|---|---|---|---|---|---|---|---|---|
| Run1 | 3.48 | 3.42 | 3.56 | 3.54 | 3.55 | 3.52 | 3.50 | 3.48 | 3.45 | 3.48 |
| Run2 | 3.46 | 3.41 | 3.54 | 3.50 | 3.54 | 3.54 | 3.50 | 3.47 | 3.46 | 3.45 |
| Run3 | 3.43 | 3.38 | 3.51 | 3.51 | 3.52 | 3.50 | 3.46 | 3.44 | 3.43 | 3.44 |

TABLE 3

| | Average flow rate (ml/min) | Standard deviation (ml/min) | RSD (%) |
|---|---|---|---|
| Run1 | 3.50 | 0.04 | 1.27 |
| Run2 | 3.49 | 0.04 | 1.29 |
| Run3 | 3.46 | 0.04 | 1.28 |

When a comparison was made between the flow rates of the ten channels, an RSD (relative standard deviation) which is an index of dispersion was about 1%, which indicates that the dispersion of the flow rates was small. As apparent from the above, in the microreactor of the present invention, a liquid can be allowed to flow almost evenly into a plurality of channels branched from one raw material tank. By the microreactor of the present invention, numbering-up can be achieved by connecting a plurality of channels to one raw material tank.

Then, using the same pressures in the raw material tanks and the same construction of the apparatus, and using part of the ten channels, the flow rates of the channels were compared. Specifically, among the ten channels, one channel, two channels, and five channels were used. The results of the measurement are shown in Table 4 below.

TABLE 4

| One channel (ml/min) | Two channels (ml/min) | Five channels (ml/min) | Ten channels (ml/min) | Average flow rate (ml/min) | Standard deviation (ml/min) | RSD (%) |
|---|---|---|---|---|---|---|
| 3.41 | 3.46 | 3.48 | 3.48 | 3.46 | 0.03 | 0.96 |

As seen from Table 4, when the number of the channels was changed without changing the pressures in the raw material tanks, the flow rates of the channels were not changed. Specifically, when the number of the channels was changed to 1, 2, 5, or 10, the flow rates of the channels were not changed.

When a conventional syringe pump or plunger pump was used, there was a need to change the flow rate of the pump according to the number of channels. Also when a part of the channels was plugged, there was a need to change the flow rate of the pump. As apparent from the above, in the conventional microreactor, numbering-up by branching the channel was difficult.

By contrast, in the microreactor of the present invention, there is no need to change the pressure in the raw material tank according to the number of channels. Further, even when a part of the channels is plugged, there is almost no effect on the flow rates of the other channels. Therefore, numbering-up by branching the channel is easy.

EXAMPLE 7

Figure 10:
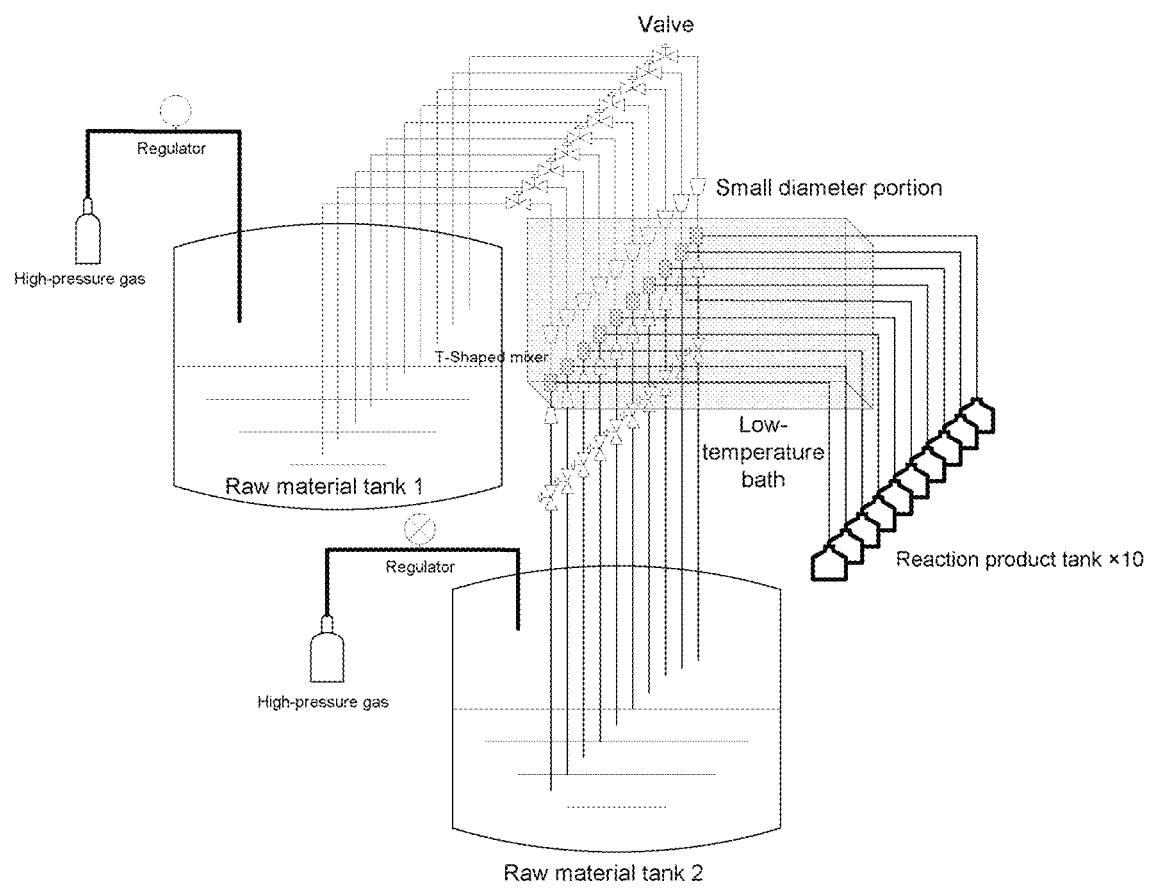
FIG. 10 shows a flow of the microreactor in Example 7.

Ten channels were connected to one raw material tank to assemble an apparatus shown in FIG. 10. Using the assembled apparatus, numbering-up for the ten channels was studied. Specifically, the apparatus shown in FIG. 10 was applied to a bromination reaction for carbazole shown in the following formula (2).

[Chemical formula 5]

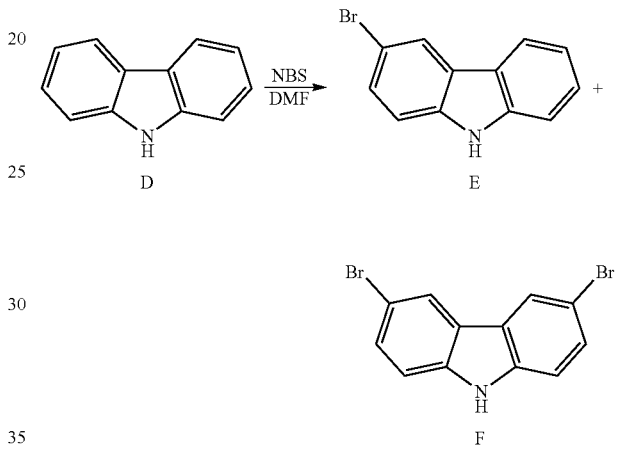

(2)

Using a mixer in which a T-shaped microchannel having an inner diameter of 1.0 mm is formed (YMC-P-0020, manufactured by YMC Co., Ltd.), two types of liquid raw materials were mixed. A pipe which connects a first raw material tank and the mixer was provided with a tube having an inner diameter of 0.25 mm and a length of 20 cm as a small diameter portion. A pipe which connects a second raw material tank and the mixer was provided with a tube having an inner diameter of 0.25 mm and a length of 10 cm as a small diameter portion. The mixer and a reaction product tank are connected through a pipe having an inner diameter of 1.0 mm and a length of 1 m.

10 g (60 mmol) of carbazole (D) was dissolved in DMF to obtain 1,000 ml of a liquid raw material. The obtained liquid raw material was stored in the first raw material tank.

7.5 g (42 mmol) of N-bromosuccinimide (NBS) was dissolved in DMF to obtain 1,000 ml of a liquid raw material. The obtained liquid raw material was stored in the second raw material tank.

The pressure in the first raw material tank was set to 56 kPa. The pressure in the second raw material tank was set to 48 kPa. The two types of liquid raw materials were sent to the mixer using the pressures in the raw material tanks. The two types of liquid raw materials mixed by the mixer were sent to a pipe. A bromination reaction proceeded in the pipe, so that bromocarbazole (E) was obtained at a reaction conversion of 80.2% on average and at an RSD of 2.1%. The results are shown in Table 5 below.

TABLE 5

| | Channel 1 | Channel 2 | Channel 3 | Channel 4 | Channel 5 | Channel 6 | Channel 7 | Channel 8 | Channel 9 | Channel 10 |
|---|---|---|---|---|---|---|---|---|---|---|
| Bromocarbazole E (%) | 82.2 | 82.6 | 78.4 | 81.8 | 77.6 | 80.8 | 80.2 | 79.7 | 78.4 | 80.6 |

EXAMPLE 8

The apparatus shown in FIG. 11 was applied to a synthesis reaction of 1-naphthylboronic acid shown in the following formula (4).

[Chemical formula 6]

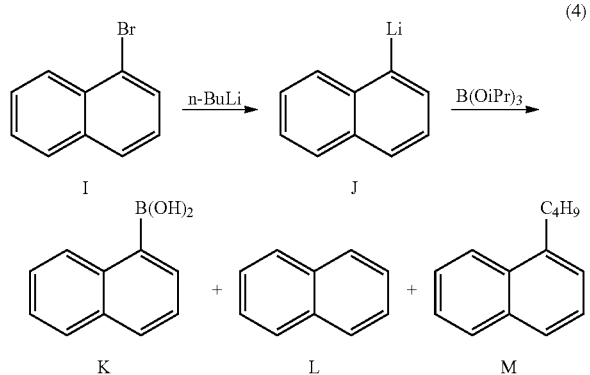

(4)

Figure 11:
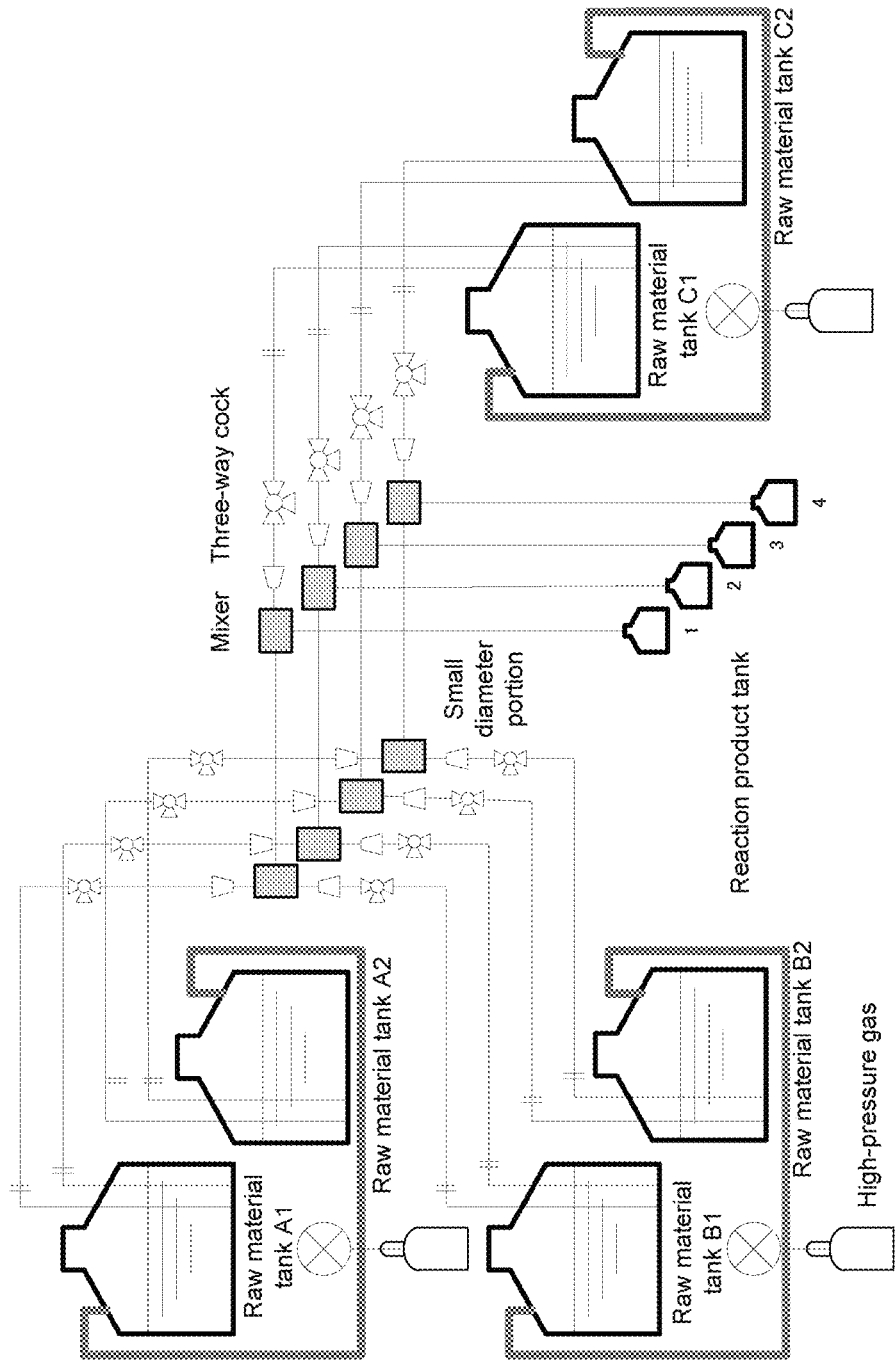
FIG. 11 shows a flow of the microreactor in Example 8.

As shown in FIG. 11, six raw material tanks for storing three types of liquid raw materials (two raw material tanks per one type of liquid raw material) were prepared. Two channels were connected to each raw material tank. That is, numbering-up using four channels per one type of liquid raw material was studied.

To the three groups of raw material tanks were connected respectively nitrogen gas feed sources. A 130 cm ⅛-inch tube made of PTFE was connected to each raw material tank. The tube was provided with a three-way cock and a small diameter portion. In the line of raw material tank A, a 1/16-inch tube made of PEEK having an inner diameter of 0.25 mm and a length of 20 cm was used as a small diameter portion. In the line of raw material tank B, a 1/16-inch tube made of PEEK having an inner diameter of 0.25 mm and a length of 5 cm was used as a small diameter portion. In the line of raw material tank C, a 1/16-inch tube made of PEEK having an inner diameter of 0.2 mm and a length of 5 cm was used as a small diameter portion.

Three types of liquid raw materials were mixed using T-shaped mixers having an inner diameter of 1 mm A mixer and another mixer were connected through a 1/16-inch tube made of PTFE having an inner diameter of 1.0 mm and a length of 20 cm. A mixer and a reaction product tank were connected through a 1/16-inch tube made of PTFE having a length of 100 cm and an inner diameter of 1.0 mm 94 ml of CPME was added to 31 ml of n-BuLi to prepare 125 ml of a 0.4 M n-BuLi hexane/CPME solution. The prepared liquid raw material was stored in raw material tanks A1, A2.

16.27 g of 1-bromonaphthalene was dissolved in 500 ml of THF to prepare a 0.15 M 1-bromonaphthalene THF solution. The prepared liquid raw material was stored in raw material tanks B1, B2.

34.24 g of triisopropyl borate was dissolved in 125 ml of THF to prepare a 0.6 M triisopropyl borate THF solution. The prepared liquid raw material was stored in raw material tanks C1, C2.

The pressure in each of the raw material tanks was set to 0.1 MPa. The three types of liquid raw materials were transferred to mixers using the pressures of gas in the raw material tanks. By reacting the three types of liquid raw materials, boronic acid was obtained. The obtained reaction product was stored in a reaction product tank. The results of the measurement with respect to the reaction product are shown in Table 6 below.

TABLE 6

| | Boronic acid K (%) | Debromination product L (%) | Bromonaphthalene I (%) | Butyl addition product M (%) |
|---|---|---|---|---|
| Reaction product tank 1 | 90.8 | 8.2 | — | — |
| Reaction product tank 2 | 90.4 | 8.6 | — | — |
| Reaction product tank 3 | 90.2 | 8.9 | — | — |
| Reaction product tank 4 | 89.2 | 9.7 | — | — |
| Average | 90.2 | 8.85 | — | — |
| Standard deviation | 0.68 | 0.64 | — | — |
| RSD | 0.76 | 7.18 | — | — |

In the all four channels, the reaction shown in the formula (4) above proceeded, so that 1-naphthylboronic acid was synthesized. The result has confirmed that the microreactor of the present invention enables numbering-up for four channels. The RSD of boronic acid was suppressed to 1% or less, and the dispersion of the results of the measurement was small.

COMPARATIVE EXAMPLE 1

Hereinbelow, Comparative Examples will be described.
By transferring liquid raw materials using syringe pumps, a synthesis reaction of naphthylboronic acid shown in the formula (4) above was conducted.

6.3 g of 1-bromonaphthalene (I) was dissolved in THF to obtain 100 ml (0.31 M) of a liquid raw material. The obtained liquid raw material was stored in a first syringe pump.

25 ml of a 1.6 M n-BuLi hexane solution was diluted with 75 ml of cyclopentyl methyl ether (CPME) to obtain 100 ml (0.4 M) of a liquid raw material. The obtained liquid raw material was stored in a second syringe pump.

11.6 g of triisopropyl borate (B(OiPr)$_3$) was dissolved in THF to obtain 100 ml (0.62 M) of a liquid raw material. The obtained liquid raw material was stored in a third syringe pump.

Using a mixer in which a T-shaped microchannel having an inner diameter of 1.0 mm is formed (YMC-P-0020, manufactured by YMC Co., Ltd.), the liquid raw materials were mixed.

The flow rate of the first, second, and third syringe pumps was set to 5 ml/min

The two types of liquid raw materials were mixed using the first mixer at room temperature to cause a lithiation in a pipe having an inner diameter of 0.5 mm and a length of 20 cm.

The two types of liquid raw materials mixed by the first mixer and the liquid raw material stored in the third raw material tank were mixed by a second mixer to effect a reaction in a pipe having an inner diameter of 1 mm and a length of 100 cm. As a result, 1-naphthylboronic acid which is an intended reaction product was obtained.

The results of an analysis by HPLC made with respect to the obtained reaction product showed that 1-naphthylboronic acid (K) was 89%, 1-bromonaphthalene (I) as a raw material was 0.3%, and naphthalene (L) which is a debromination product was 6.8%. A butyl addition product (M), which is likely to be formed under high temperature conditions, was 1.9%.

COMPARATIVE EXAMPLE 2

Substantially the same measurement as in Example 5 above was performed except that the small diameter portion of the apparatus shown in FIG. 8 was removed. The measurement has proved the effect obtained by providing the apparatus with the small diameter portion.

Water was placed in each raw material tank in the same manner as in Example 5 above. The pressure of the gas fed to the raw material tank was set to 50 kPa. The valve of channel A2 was opened 30 seconds after the valve of channel A1 was opened. The valve of channel B was opened 30 seconds after the valve of channel A2 was opened. The valves were closed 10 minutes respectively after the valves were opened. After the valves were closed, weights of the reaction product tanks were measured. From the measured weights of the reaction product tanks, a flow rate of each channel was determined. The results of the measurement are shown in Table 7 below.

TABLE 7

| Channel A1 (ml/min) | Channel A2 (ml/min) | Channel B (ml/min) | Average flow rate (ml/min) | Standard deviation (ml/min) | RSD (%) |
|---|---|---|---|---|---|
| 25.8 | 25.6 | 29.9 | 27.1 | 2.43 | 8.96 |

As can be seen from the results shown in Table 7, the dispersion of the flow rate in Example 5 is smaller than that in Comparative Example 2. That is, in the case where the pipe which connects the raw material tank and the reaction product tank is provided with a small diameter portion, the dispersion of the flow rate is smaller than that in the case where the small diameter portion is removed. As apparent from the above, by providing a plurality of channels connected to the raw material tank with a small diameter portion, the dispersion of the flow rates of the channels is reduced.

DESCRIPTION OF THE REFERENCE NUMERALS 10, 110, 210, 310: Microreactor
12, 112a, 112b, 112c, 212a, 212b, 212c, 312: Raw material tank
14: Constant temperature bath
16, 116, 216, 316: Reaction product tank
18, 20, 118a, 118b, 120, 218a, 218b, 218c, 218d, 220, 318a, 318b, 320: Pipe
19a, 19b: Connector
22, 122a, 122b, 222a, 222b, 222c, 322: Nitrogen feed pipe
24, 124a, 124b, 224a, 224b, 224c, 324: Pressure regulating valve
26, 126a, 126b, 226a, 226b, 226c: On-off valve
28, 128a, 128b, 228a, 228b, 228c, 328, 400, 410: Small diameter portion
114, 214a, 214b, 314: Mixer

The invention claimed is:

1. A microreactor comprising a transfer means for transferring a liquid raw material using a pressure of a gas and a raw material tank for storing the liquid raw material,
wherein the transfer means transfers the liquid raw material stored in the raw material tank using the pressure of the gas in the raw material tank.

2. The microreactor according to claim 1, further comprising a gas feeding means for feeding a gas into the raw material tank.

3. The microreactor according to claim 2, further comprising a pressure regulating means for regulating the pressure of the gas in the raw material tank.

4. The microreactor according to claim 2, wherein the raw material tank comprises a pressure tank.

5. The microreactor according to claim 2, further comprising a mixer for mixing the liquid raw material and another raw material with each other,
wherein a pipe which connects the raw material tank and the mixer is provided with a small diameter portion.

6. The microreactor according to claim 1, further comprising a pressure regulating means for regulating the pressure of the gas in the raw material tank.

7. The microreactor according to claim 6, wherein the raw material tank comprises a pressure tank.

8. The microreactor according to claim 6, further comprising a mixer for mixing the liquid raw material and another raw material with each other,
wherein a pipe which connects the raw material tank and the mixer is provided with a small diameter portion.

9. The microreactor according to claim 1, wherein the raw material tank comprises a pressure tank.

10. The microreactor according to claim 9, further comprising a mixer for mixing the liquid raw material and another raw material with each other,
wherein a pipe which connects the raw material tank and the mixer is provided with a small diameter portion.

11. The microreactor according to claim 1, further comprising a mixer for mixing the liquid raw material and another raw material with each other,
wherein a pipe which connects the raw material tank and the mixer is provided with a small diameter portion.

12. The microreactor according to claim 11, wherein the pressure in a pipe which connects the raw material tank and the small diameter portion is 1.5 MPa or less.

13. The microreactor according to claim 11, further comprising a plurality of the raw material tanks, wherein the liquid raw materials transferred from the raw material tanks are mixed by the mixer.

14. The microreactor according to claim 11, wherein the small diameter portion comprises a tube having an inner diameter smaller than the inner diameter of a pipe positioned upstream and/or downstream of the tube.

15. The microreactor according to claim 14, wherein the pressure in a pipe which connects the raw material tank and the small diameter portion is 1.5 MPa or less.

16. The microreactor according to claim 14, further comprising a plurality of the raw material tanks, wherein the liquid raw materials transferred from the raw material tanks are mixed by the mixer.

17. The microreactor according to claim 1, wherein the gas is nitrogen.

18. A microchemical plant comprising a plurality of microreactors according to claim 1, wherein the microreactors are connected in parallel.

19. A microchemical plant comprising a plurality of the microreactors according to claim 1, wherein a plurality of channels are connected to the raw material tank.

* * * * *